(12) United States Patent
Matsumoto et al.

(10) Patent No.: US 7,160,689 B2
(45) Date of Patent: Jan. 9, 2007

(54) PRETREATMENT INSTRUMENT OF SALIVA AND PRETREATMENT METHOD OF SALIVA

(75) Inventors: Yuko Matsumoto, Tokyo (JP); Yumiko Kobayashi, Tokyo (JP); Junichi Okada, Tokyo (JP)

(73) Assignee: GC Corporation, Tokyo (JP)

( * ) Notice: Subject to any disclaimer, the term of this patent is extended or adjusted under 35 U.S.C. 154(b) by 720 days.

(21) Appl. No.: 10/163,614

(22) Filed: Jun. 7, 2002

(65) Prior Publication Data

US 2002/0197738 A1    Dec. 26, 2002

(30) Foreign Application Priority Data

Jun. 21, 2001  (JP) .............................. 2001-188068

(51) Int. Cl.
*G01N 33/53* (2006.01)

(52) U.S. Cl. ............... 435/7.34; 435/287.1; 435/288.1; 604/1; 604/2; 604/3; 604/363; 422/61; 422/99; 422/93; 422/44; 424/537; 436/518

(58) Field of Classification Search ............... 604/1–3, 604/363; 422/50, 55–60, 61, 99, 93, 44; 424/93.44, 537; 206/361; 436/518; 435/7.34, 435/287.1, 288.1
See application file for complete search history.

(56) References Cited

U.S. PATENT DOCUMENTS

| | | | | |
|---|---|---|---|---|
| 3,674,007 A | * | 7/1972 | Freis ........................... 600/572 |
| 3,776,220 A | * | 12/1973 | Monaghan ................... 600/572 |
| 3,913,562 A | * | 10/1975 | Moore et al. ............. 435/307.1 |
| 3,915,806 A | * | 10/1975 | Horlach .................... 435/307.1 |
| 4,175,439 A | * | 11/1979 | Laker ...................... 73/864.72 |
| 4,359,455 A | * | 11/1982 | Nakamura et al. ............. 435/34 |
| 4,387,725 A | * | 6/1983 | Mull ........................... 600/572 |
| 4,582,795 A | * | 4/1986 | Shibuya et al. ................ 435/34 |
| 4,637,061 A | * | 1/1987 | Riese ........................... 383/38 |

(Continued)

FOREIGN PATENT DOCUMENTS

EP    0 155 747    9/1985

(Continued)

OTHER PUBLICATIONS

U.S. Appl. No. 10/299,800, filed Nov. 20, 2002, Matsumoto.

(Continued)

*Primary Examiner*—Bao-Thuy L. Nguyen
(74) *Attorney, Agent, or Firm*—Oblon, Spivak, McClelland, Maier & Neustadt, P.C.

(57) ABSTRACT

In a pretreatment instrument and a pretreatment method of saliva, used for identification and quantitation of *Streptococcus mutans* in saliva by the immunochromatographic method utilizing an antigen-antibody reaction, the instrument includes a swab and a mixing container for saliva and a treatment liquid, the swab having a stick and a soft synthetic resin-made sponge capable of absorbing a predetermined amount or more of saliva, and the mixing container being made of a transparent or translucent soft synthetic resin and comprising a bag-like portion formed integrally with and continuously to a constricted portion as the end of a tapering introduction portion having an opening thoroughly larger than the sponge, wherein the constricted portion and the bag-like portion have elasticity such that the sponge can be squashed by a finger pressure in a state that the sponge is inserted therein; the constricted portion has a width such that a pressure can be applied by fingers and has a shape such that when the sponge is taken out in a squashed state by the finger pressure, a minimum amount necessary for the pretreatment or more of the saliva can be squeezed out.

13 Claims, 3 Drawing Sheets

U.S. PATENT DOCUMENTS

| | | | | |
|---|---|---|---|---|
| 4,707,450 | A | * | 11/1987 | Nason ........................ 600/572 |
| 4,789,639 | A | * | 12/1988 | Fleming ..................... 436/178 |
| 4,956,301 | A | * | 9/1990 | Ismail et al. .................. 436/87 |
| 5,013,667 | A | * | 5/1991 | Lynn et al. .................. 436/126 |
| 5,028,543 | A | * | 7/1991 | Finch et al. ................ 436/124 |
| 5,085,781 | A | * | 2/1992 | Tsuru et al. ................ 210/692 |
| 5,152,742 | A | * | 10/1992 | Simpson ........................ 604/3 |
| 5,260,031 | A | * | 11/1993 | Seymour .................... 422/101 |
| 5,431,884 | A | * | 7/1995 | McDonough et al. ....... 422/101 |
| 6,015,681 | A | * | 1/2000 | Ralls et al. ................ 435/7.32 |
| 6,406,922 | B1 | * | 6/2002 | Casterlin et al. ............ 436/518 |
| 6,423,550 | B1 | * | 7/2002 | Jenkins et al. .............. 436/518 |
| 6,516,947 | B1 | * | 2/2003 | Van Dyke et al. .......... 206/361 |
| 6,727,073 | B1 | * | 4/2004 | Moore et al. .............. 435/7.32 |
| 6,863,866 | B1 | * | 3/2005 | Kelly et al. .................. 422/56 |

FOREIGN PATENT DOCUMENTS

| | | |
|---|---|---|
| EP | 0 621 232 | 10/1994 |
| WO | WO 94/18892 | 9/1994 |
| WO | WO 95/30484 | 11/1995 |
| WO | WO 98/14276 | 4/1998 |

OTHER PUBLICATIONS

U.S. Appl. No. 10/429,767, filed May 6, 2003, Matsumoto et al.
U.S. Appl. No. 10/163,614, filed Jun. 7, 2002, Matsumoto et al.

* cited by examiner

PRETREATMENT INSTRUMENT OF SALIVA AND PRETREATMENT METHOD OF SALIVA

BACKGROUND OF THE INVENTION

1. Field of the Invention

The present invention relates to a pretreatment instrument of saliva and a pretreatment method of saliva, used for identification and quantitation of *Streptococcus mutans* as one of cariogenic bacteria in human saliva by the immunochromatographic method utilizing an antigen-antibody reaction.

2. Description of the Conventional Art

It is known that there is a close relation between the presence of *Streptococcus mutans* and the generation of dental caries in a human mouth. If the presence or absence of *Streptococcus mutans* and the amount thereof in the human mouth can be simply examined, it is possible to grasp an incidence risk and the present incidence status, resulting in giving benefits to an extremely large number of people.

Hitherto, there has been employed an examination utilizing an antigen-antibody reaction in examining bacteria. For example, the enzyme labeled antibody method is a method for effecting the identification and quantitation by means of a density of color generation using an enzyme. However, this method was required to use a special cleaning device and complicated and precise operations for dealing with an antibody and a sample and to introduce incubation for the enzymatic reaction. Further, the immunofluorescent antibody method is a method for labeling an antibody with a fluorescent dye and specifically dyeing an antigen reacted with the antibody. However, this method is not a general method because a fluorescence microscope is needed as an assaying device.

For these reasons, a number of methods have been proposed as the method for simply utilizing the antigen-antibody reaction. For example, the assaying method utilizing chromatography, as disclosed in U.S. Pat. Nos. 5,591,645, 4,855,240, 4,435,504 and 4,980,298 and Japanese Patent Laid-Open Nos. 145459/1986 and 160388/1994, is a method with excellent simplicity, by which the presence or absence of an antigen and the amount thereof can be known only by incorporating a collected body fluid into a test solution containing the antigen for the purpose of the identification and quantitation and infiltrating the mixture into an examination instrument. Such a method is generally called an immunochromatographic method. In this method, a specified antibody that attaches to only a target antigen (this antibody will be hereinafter referred to as "specific antibody") is infiltrated into one end of a porous membrane (a pore diameter: several tens μm) such as nitrocellulose, and in the middle of the porous membrane, another specific antibody similarly attaching to only a specified antigen is infiltrated in a strip-like form and immobilized in the porous membrane. The specific antibody as infiltrated into the one end of the porous membrane is previously colored by particles of, e.g., gold colloid. When a sample solution is infiltrated on the one end of the porous membrane wherein this specific antibody is present, if an antigen reactive with the specific antibody is present in the sample solution, the antigen is coupled with the specific antibody and moves in the porous membrane by capillarity in a state having the colored particles attached thereto towards the side opposite to the one end at which the sample solution is infiltrated. On the way of the movement, when the antigen passes through a place where another specific antibody is immobilized in a strip-like form, the antigen is trapped by the specific antibody in the porous membrane, whereby a strip-like blotting appears on the porous membrane. Thus, it is possible to know that the target antigen is present in the sample along with the amount thereof.

If such technique were applied, it would appear to realize the identification and quantitation of *Streptococcus mutans* in the mouth. Actually, however, this technique has not yet been put into practical use because it involves the following problems. That is, in principle, the sample that can be used in the immunochromatographic method must be able to pass through the porous membrane by capillarity. However, since a major sample used for the examination of bacteria in the mouth, such as *Streptococcus mutans*, is saliva, a viscous substance present in the saliva, called as mucin, plugs the pores of the porous membrane. Also, the mucin functions to agglutinate epithelial attachment cells having peeled off from an oral mucous surface and existing in the saliva. Accordingly, these substances plug the pores of the porous membrane, so that the *Streptococcus mutans* cannot pass through the porous membrane.

In addition, there is present other problem than the mucin, which makes the assay of *Streptococcus mutans* difficult. That is, though the subjective *Streptococcus mutans* is a bacterium having a diameter of about 1 μm in a single state, because it is a *streptococcus*, it often forms a chain of 10 to 20 or more, which will be a possible factor for inhibiting the movement in the porous membrane. Moreover, the *Streptococcus mutans* often produces viscous glucan from sucrose in foods and causes vigorous agglutination. The chain and agglutination of the *Streptococcus mutans* cause not only clogging of the porous membrane but also reduction of the surface area of the *streptococcus*, thereby influencing the number of antigens present on the surface of the *Streptococcus mutans*, resulting in lowering in the precision of the assay.

Thus, we, the present inventors, previously proposed a pretreatment instrument of saliva, which during identification and quantitation of *Streptococcus mutans* as one of cariogenic bacteria in human saliva by the immunochromatographic method, dissolves mucin in the saliva by a simple method, thereby enabling not only to inhibit agglutination of epithelial attachment cells by the mucin but also to suppress agglutination of *Streptococcus mutans* (see Japanese Patent Application No. 2001-92769).

That is, the present inventors found the following matters: when the saliva is treated with an aqueous sodium hydroxide solution, the mucin and glucan in the saliva are dissolved, thereby inhibiting the agglutination of the epithelial attachment cells, or acting to an outer membrane of the *Streptococcus mutans* to enable to suppress the agglutination of the *Streptococcus mutans*; also, when the saliva is treated with a specific acidic aqueous solution, chaining of the *Streptococcus mutans* is inhibited, thereby enabling to suppress the agglutination of the *Streptococcus mutans*; and in addition, when the saliva is treated with a mixture of the aqueous sodium hydroxide solution or acidic aqueous solution and a specific surfactant, proteins present in the *Streptococcus mutans* are solubilized, whereby the *Streptococcus mutans* can smoothly pass through the porous membrane.

However, when using such a pretreatment instrument of saliva, in order to mix the saliva with the aqueous sodium hydroxide solution or the specific acidic aqueous solution, or the mixture of the aqueous sodium hydroxide solution or the specific acidic aqueous solution and the specific surfactant, efficiently within a short period of time such that the *Streptococcus mutans* can be identified and quantitated by the immunochromatographic method, it is necessary to use a mixing device having a strong mixing action such as an electromotive mixer. However, since the amount of the saliva collected from a subject for the examination is generally very small, a specific mixing device must be used. In the case where such a specific mixing device is not available, it is impossible to identify and quantitate the *Streptococcus mutans*. On the other hand, the mixing device must be cleaned up every time after it has been used once, leading to a very troublesome operation.

SUMMARY OF THE INVENTION

Thus, the invention is aimed to provide a pretreatment instrument of saliva and a pretreatment method of saliva, by which the pretreatment for mixing saliva with the aqueous sodium hydroxide solution or the specific acidic aqueous solution, or the mixture of the aqueous sodium hydroxide solution or the specific acidic aqueous solution and the specific surfactant, can be effected without using a specific mixing device.

In order to achieve the above-described aim, we, the present inventors made extensive and intensive investigations. As a result, it has been found that the aim can be achieved in the following manner. That is, when, using a pretreatment instrument of saliva comprising a swab and a mixing container for saliva and a treatment liquid, the swab comprising a stick at a front end of which is fixed a soft synthetic resin-made sponge having a predetermined shape condition and being capable of absorbing a predetermined or more amount of saliva, and the mixing container having a predetermined shape and being made of an elastic, transparent or translucent soft synthetic resin, the swab in which the soft synthetic resin-made sponge has absorbed saliva is inserted within a bag-like portion of the mixing container from the side of the soft synthetic resin-made sponge; either one of an aqueous sodium hydroxide solution or an acidic aqueous solution is added dropwise within the mixing container under that state; a finger pressure is then applied to the bag-like portion, thereby squashing the soft synthetic resin-made sponge; and rapid discharge and inhalation of the saliva from and into the soft synthetic resin-made sponge are repeated through the foregoing operations, the saliva can be mixed with the liquid added dropwise by a rapid stirring effect. Thus, when the swab is then taken out from the mixing container while applying a finger pressure to a constricted portion, the liquid absorbed in the soft synthetic resin-made sponge is squeezed out within the bag-like portion, and the other aqueous solution is added dropwise thereto and mixed therewith. Alternatively, after the other aqueous solution has been added dropwise and mixed, the swab is taken out from the mixing container while applying a finger pressure to the constricted portion, thereby squeezing out the liquid absorbed in the soft synthetic resin-made sponge within the bag-like portion. Then, the invention has been accomplished.

Specifically, the invention relates to a pretreatment instrument comprising a swab and a mixing container for saliva and a treatment liquid, the swab comprising a stick at a front end of which is fixed a soft synthetic resin-made sponge capable of absorbing a predetermined amount or more of saliva, and the mixing container being made of a transparent or translucent soft synthetic resin and comprising a bag-like portion formed integrally with and continuously to a constricted portion as the end of a tapering introduction portion having an opening thoroughly larger than the soft synthetic resin-made sponge of the swab, into which the soft synthetic resin-made sponge can be inserted, wherein the constricted portion and the bag-like portion in the mixing container have elasticity such that the soft synthetic resin-made sponge can be squashed by a finger pressure in a state that the soft synthetic resin-made sponge is inserted within the constricted portion and the bag-like portion; the constricted portion has a width such that a pressure can be applied by fingers and has a shape such that when the soft synthetic resin-made sponge of the swab is taken out in a squashed state by the finger pressure, a minimum amount necessary for the pretreatment of saliva or more amount of the saliva can be squeezed out.

Also, the invention relates to a pretreatment method of saliva for identification and quantitation of *Streptococcus mutans* by the immunochromatographic method, which comprises inserting a swab comprising a stick at a front end of which is fixed a soft synthetic resin-made sponge having saliva absorbed therein into a bag-like portion of a mixing container made of a transparent or translucent soft synthetic resin from the side of the soft synthetic resin-made sponge, the mixing container comprising the bag-like portion formed integrally with and continuously to a constricted portion as an end point of a tapering introduction portion having an opening thoroughly larger than the soft synthetic resin-made sponge of the swab; adding dropwise either one of an aqueous sodium hydroxide solution or an acidic aqueous solution from the opening into the mixing container under that state; applying a finger pressure to the bag-like portion and squashing the soft synthetic resin-made sponge, thereby mixing the saliva with the liquid added dropwise; taking out the swab from the mixing container while applying a finger pressure to the constricted portion, thereby squeezing out the liquid absorbed in the soft synthetic resin-made sponge within the bag-like portion; and adding dropwise the other of the aqueous sodium hydroxide solution or the acidic aqueous solution thereto from the opening within the mixing container and mixing therewith; alternatively, squashing the soft synthetic resin-made sponge, thereby mixing the saliva with the liquid added dropwise; adding dropwise the other of the aqueous sodium hydroxide solution or the acidic aqueous solution thereto from the opening within the mixing container and mixing therewith; and taking out the swab from the mixing container while applying a finger pressure to the constricted portion, thereby squeezing out the liquid absorbed in the soft synthetic resin-made sponge within the bag-like portion.

And, in the pretreatment instrument of saliva, it is preferred that the soft synthetic resin-made sponge is an open-cell sponge having a cell diameter of 50 to 400 µm; and that a lower limit line as a standard of a minimum amount of the liquid accommodated within the bag-like portion necessary for the pretreatment of saliva is provided in a position with a predetermined distance from a bottom portion of the bag-like portion. Further, in the pretreatment method of saliva, it is preferred that an aqueous solution further mixed with a pH indicator having a color transition range at a pH from 5 to 9 is used as the aqueous sodium hydroxide solution or the acidic aqueous solution; that a pH indicator having a color transition range at a pH from 5 to 9 is added dropwise and mixed after the dropwise addition of either one of the aqueous sodium hydroxide solution or the acidic aqueous solution but prior to the dropwise addition of the other of the aqueous sodium hydroxide solution or the acidic aqueous solution; that as the pH indicator having a color transition range at a pH from 5 to 9, employable is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein; that as the aqueous sodium hydroxide solution or the acidic aqueous solution, used is an aqueous solution further mixed with a nonionic surfactant and/or an ampholytic surfactant; that a nonionic surfactant and/or an ampholytic surfactant is added dropwise and mixed at an arbitrary timing; and that the acidic aqueous solution is a tris(hydroxymethyl)aminomethane buffer solution containing tartaric acid and/or citric acid, and the nonionic surfactant and/or the ampholytic surfactant is one or two or more members selected from the group consisting polyethylene glycol monooctylphenyl ether, n-octyl-β-D-glucoside, n-heptyl-β-D-thioglucoside, n-octyl-β-D-thioglucoside, nonyl phenoxypolyethoxy ethanol, octyl phenoxypolyethoxy ethanol, polyoxyethylene sorbitan monooleate, 3-[(3-cholamidopropyl)-dimethylammonio]-1-propane sulfonate, and 3-[(3-cholamidopropyl)dimethylammonio]-1-hydroxypropane sulfonate.

DESCRIPTION OF THE PREFERRED EMBODIMENTS

The pretreatment instrument of saliva and the pretreatment method of saliva according to the present invention will be described below in detail with reference to the drawings.

Figure 1:
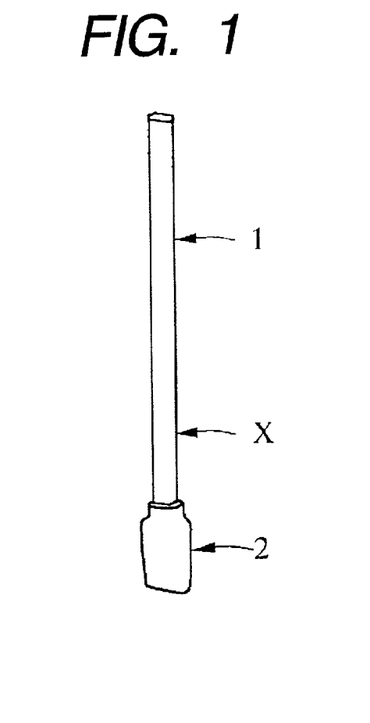
FIG. 1 is a perspective view showing one embodiment of a swab of the pretreatment instrument of saliva according to the present invention.
Figure 2:
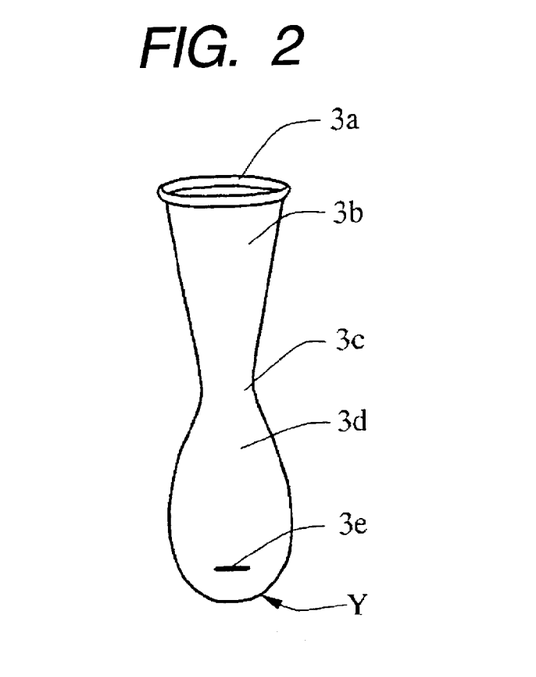
FIG. 2 is a perspective view showing one embodiment of a mixing container of the pretreatment instrument of saliva according to the present invention.
Figure 3:
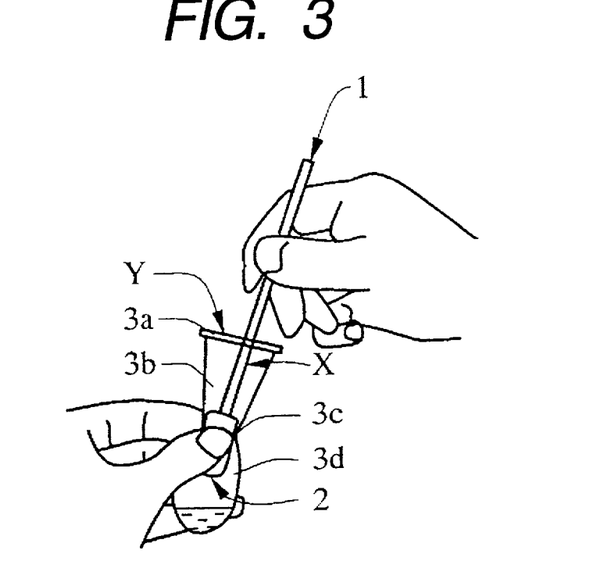
FIG. 3 is an explanatory drawing showing the state in which, in the pretreatment method of saliva according to the present invention, a liquid absorbed in a soft synthetic resin-made sponge of a swab is squeezed out from the soft synthetic resin-made sponge.
Figure 4:
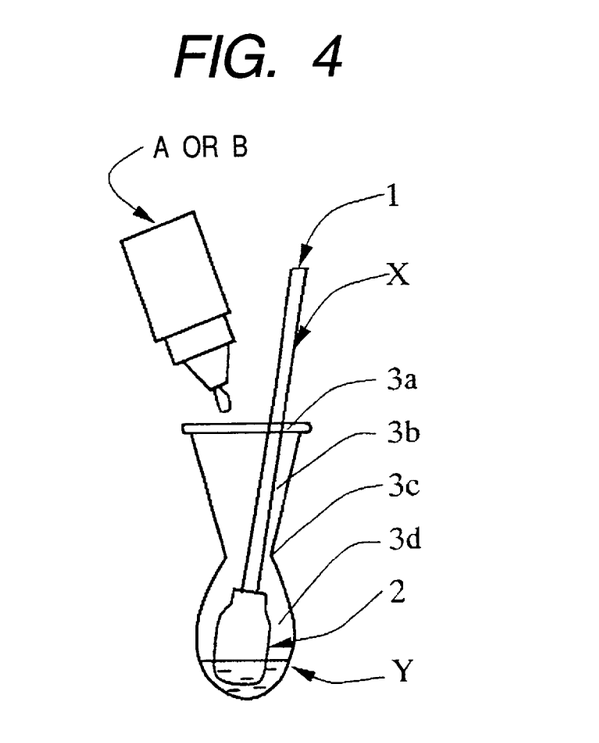
FIG. 4 is an explanatory drawing showing the state in which, in the pretreatment method of saliva according to the present invention, a soft synthetic resin-made sponge of a swab having saliva absorbed therein is inserted within a bag-like portion of a mixing container, and either one of an alkaline aqueous solution or an acidic aqueous solution is added dropwise.
Figure 5:
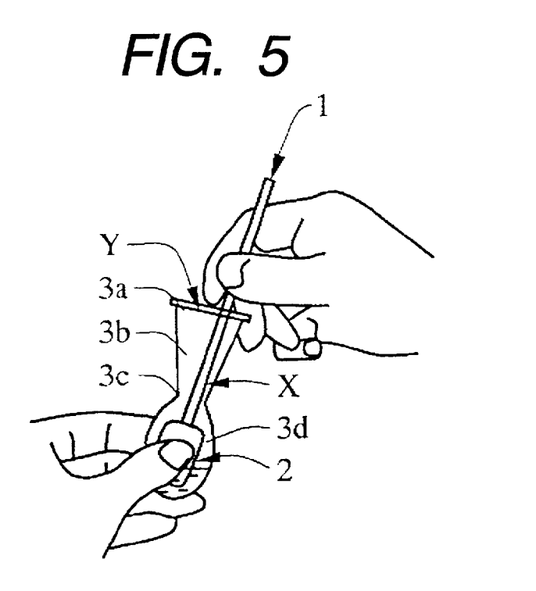
FIG. 5 is an explanatory drawing showing the state in which, in the pretreatment method of saliva according to the present invention, a soft synthetic resin-made sponge of a swab having saliva absorbed therein is inserted within a bag-like portion of a mixing container, either one of an alkaline aqueous solution or an acidic aqueous solution is added dropwise, and then a finger pressure is applied to the bag-like portion, thereby mixing saliva with the liquid added dropwise.
Figure 6:
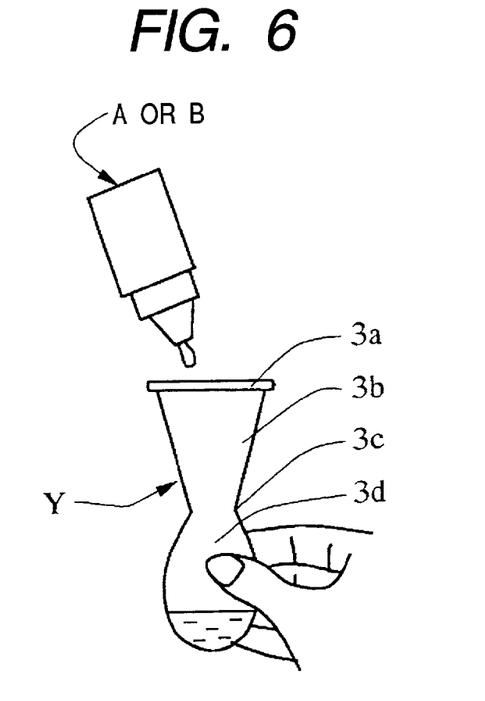
FIG. 6 is an explanatory drawing showing the state in which, in the pretreatment method of saliva according to the present invention, either one of an alkaline aqueous solution or an acidic aqueous solution is added dropwise to a mixed solution of saliva and a liquid added dropwise within a bag-like portion of a mixing container.

FIG. 1 is a perspective view showing one embodiment of a swab of the pretreatment instrument of saliva according to the present invention; FIG. 2 is a perspective view showing one embodiment of a mixing container of the pretreatment instrument of saliva according to the present invention; FIG. 3 is an explanatory drawing showing the state in which, in the pretreatment method of saliva according to the present invention, a liquid absorbed in a soft synthetic resin-made sponge of a swab is squeezed out from the soft synthetic resin-made sponge; FIG. 4 is an explanatory drawing showing the state in which, in the pretreatment method of saliva according to the present invention, a soft synthetic resin-made sponge of a swab having saliva absorbed therein is inserted within a bag-like portion of a mixing container, and either one of an alkaline aqueous solution or an acidic aqueous solution is added dropwise; FIG. 5 is an explanatory drawing showing the state in which, in the pretreatment method of saliva according to the present invention, a soft synthetic resin-made sponge of a swab having saliva absorbed therein is inserted within a bag-like portion of a mixing container, either one of an alkaline aqueous solution or an acidic aqueous solution is added dropwise, and a finger pressure is applied to the bag-like portion, thereby mixing saliva with the liquid added dropwise; and FIG. 6 is an explanatory drawing showing the state in which, in the pretreatment method of saliva according to the present invention, either one of an alkaline aqueous solution or an acidic aqueous solution is added dropwise to a mixed solution of saliva and a liquid added dropwise within a bag-like portion of a mixing container.

In the drawings, a numeral reference X is a swab constituting one side of the pretreatment instrument of saliva according to the present invention, and as shown in FIG. 1, a soft synthetic resin-made sponge 2 capable of absorbing a predetermined or more amount (usually 1 cc or more) of saliva is fixed at a front end of a stick 1. A length of the swab X is preferably about 5 to 10 cm longer than that of a mixing container Y as described later.

It is preferred that the stick 1 is made of a synthetic resin such as a polypropylene resin, or a natural wood or bamboo, which has a strength to some extent and is relatively light in weight, and from which a plasticizer or the like does not elute.

It is preferred that the soft synthetic resin-made sponge 2 is an open-cell sponge such that an effect for mixing the absorbed saliva with a liquid added dropwise is enhanced; and that a raw material thereof is polyurethane from which the plasticizer or the like does not elute. The soft synthetic resin-made sponge 2 preferably has a cell diameter of 50 to 400 μm from the standpoint of attaining the purposes of easiness in the production and cutting off the chain of the *Streptococcus mutans*. It is preferred that the soft synthetic resin-made sponge 2 has such a shape that almost all of the absorbed saliva can be squeezed in a constricted portion 3c of the mixing container Y as described later. Accordingly, it is preferred that a major part of the outer surface of the soft synthetic resin-made sponge 2 is parallel to the longitudianl direction of the stick 1 and has no irregularities and that a portion of the soft synthetic resin-made sponge 2 where its outer periphery length in the lateral cross-section perpendicular to the longitudinal direction of the stick 1 is longer than an inner periphery length of the constricted portion 3c of the mixing container Y occupies a major part in the longitudinal direction of the stick 1. For example, the shape of the soft synthetic resin-made sponge 2 is preferably of a cylindrical type, a polygonal pillar type such as a quadrangular pole pillar, or a plate-like type such as a rectangular type as in the embodiment shown in the drawings. The soft synthetic resin-made sponge 2 may also be of a ball type, an artillery shell type, or a teardrop type.

A numeral reference Y is a mixing container for saliva and a treatment liquid, which constitutes the other side of the pretreatment instrument of saliva according to the present invention. As shown in FIG. 2, the mixing container Y is made of a transparent or translucent soft synthetic resin and comprises a bag-like portion 3d formed integrally with and continuously to a constricted portion 3c as an end point of a tapering introduction portion 3b having an opening 3a thoroughly larger than the soft synthetic resin-made sponge 2 of the swab X, into which the soft synthetic resin-made sponge 2 can be inserted. The constricted portion 3c and the bag-like portion 3d have elasticity such that the soft synthetic resin-made sponge 2 can be squashed by a finger pressure in a state that the soft synthetic resin-made sponge 2 of the swab X is inserted within the constricted portion 3c and the bag-like portion 3d. The constricted portion 3c has a width such that a pressure can be applied by fingers and has a shape such that when the soft synthetic resin-made sponge 2 of the swab X is taken out in a squashed state by the finger pressure, a minimum amount necessary for the pretreatment of saliva or more amount of the saliva can be squeezed out. And, it is preferred that a lower limit line 3e as a standard of a minimum amount of the liquid accommodated within the bag-like portion 3d necessary for the pretreatment of saliva is provided in a position with a predetermined distance from a bottom portion of the bag-like portion 3d.

In order to carry out the pretreatment method of saliva using the pretreatment instrument of saliva comprising the swab X and the mixing container Y according to the present invention, first of all, a subject is made to chew a gum or the like, thereby causing to secrete enough saliva. Then, the swab X is inserted into a mouth from the side of the soft synthetic resin-made sponge 2 which is then squashed with a tongue or lips, thereby the saliva being absorbed in the soft synthetic resin-made sponge 2 of the swab X. Alternatively, the subject is made to spit out the saliva into a cup or the like, thereby the saliva being absorbed in the soft synthetic resin-made sponge 2 of the swab X.

Next, the swab X having the saliva absorbed in the soft synthetic resin-made sponge 2 is inserted into the mixing container Y from the side of the soft synthetic resin-made sponge 2. Thereafter, as shown in FIG. 3, in a state that the soft synthetic resin-made sponge 2 is inserted within the constricted portion 3c of the mixing container Y, the swab X is taken out from the mixing container while applying a finger pressure to the constricted portion 3c, thereby squeezing out the saliva absorbed in the soft synthetic resin-made sponge 2 into the bag-like portion 3d and confirming that a minimum amount necessary for the pretreatment of saliva or more amount of the saliva is collected. This operation can be achieved easily when the lower limit line 3e as a standard of a minimum amount of the saliva accommodated within the bag-like portion 3d necessary for the pretreatment of saliva is provided in a position with a predetermined distance from a bottom portion of the bag-like portion 3d. In the case where the amount of the saliva is less than the minimum amount necessary for the pretreatment of saliva, the above-described operation is repeated, thereby replenishing the saliva. Thereafter, the soft synthetic resin-made sponge 2 of the swab X is again inserted into the bag-like portion 3d having the saliva accommodated therein.

This operation is not necessary in the case where it is already known that the amount of the saliva absorbed in the soft synthetic resin-made sponge 2 of the swab X is sufficient for carrying out the pretreatment of saliva.

Thereafter, as shown in FIG. 4, either one of an aqueous sodium hydroxide solution A or an acidic aqueous solution B is added dropwise within the mixing container Y from the opening 3a. Then, as shown in FIG. 5, when an operation of squashing the soft synthetic resin-made sponge 2 by applying a finger pressure to the bag-like portion 3d is repeated, the saliva and the aqueous sodium hydroxide solution A or the acidic aqueous solution B added dropwise are strongly stirred by rapid discharge and inhalation from and into the soft synthetic resin-made sponge 2. Accordingly, it is possible to easily mix the saliva with the aqueous sodium hydroxide solution A or the acidic aqueous solution B added dropwise. Incidentally, it is preferred that the squashing operation of the soft synthetic resin-made sponge 2 is repeated ten times or more.

In order to collect the saliva thus mixed with the aqueous sodium hydroxide solution A or the acidic aqueous solution B added dropwise from the soft synthetic resin-made sponge 2, the saliva mixed with the aqueous sodium hydroxide solution A or the acidic aqueous solution B added dropwise, which has been absorbed in the soft synthetic resin-made sponge 2, is squeezed out within the bag-like portion 3d by the operation as shown in FIG. 3, namely, by taking out the swab X from the mixing container Y while applying a finger pressure to the constricted portion 3c in a state that the soft synthetic resin-made sponge 2 of the swab X is inserted in the constricted portion 3c of the mixing container Y; and then, as shown in FIG. 6, the other of the aqueous sodium hydroxide solution A or the acidic aqueous solution B is added dropwise into the bag-like portion 3d, and the mixing container Y is shaken, thereby mixing the saliva with the other of the aqueous sodium hydroxide solution A or the acidic aqueous solution B added dropwise. During this operation, it is preferred that the treated saliva has a pH of 5 to 9 as described later. Accordingly, at least either one of the aqueous sodium hydroxide solution A or the acidic aqueous solution B added dropwise is mixed with a pH indicator having a color transition range at a pH from 5 to 9. Alternatively, in the case where at least either one of the aqueous sodium hydroxide solution A or the acidic aqueous solution B added dropwise is not mixed with a pH indicator having a color transition range at a pH from 5 to 9, a pH indicator having a color transition range at a pH from 5 to 9 is added dropwise and mixed after the dropwise addition of either one of the aqueous sodium hydroxide solution A or the acidic aqueous solution B but prior to the dropwise addition of the other of the aqueous sodium hydroxide solution A or the acidic aqueous solution B. Thus, a pH value can be confirmed by the change in color of the treatment liquid of saliva, and hence, such is preferred.

As the pH indicator having a color transition range at a pH from 5 to 9, preferred is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

Further, prior to the operation for collecting the saliva mixed with the aqueous sodium hydroxide solution A or the acidic aqueous solution B added dropwise, as shown in FIG. 4, the other of the aqueous sodium hydroxide solution A or the acidic aqueous solution B is added dropwise into the bag-like portion 3d, and the mixing container Y is shaken, thereby mixing the saliva with the other of the aqueous sodium hydroxide solution A or the acidic aqueous solution B added dropwise, or as shown in FIG. 5, the operation for squashing the soft synthetic resin-made sponge 2 while applying a finger pressure to the bag-like portion 3d is repeated, thereby achieving the mixing. Thereafter, the saliva mixed with the aqueous sodium hydroxide solution A or the acidic aqueous solution B added dropwise, which has been absorbed in the soft synthetic resin-made sponge 2, may be squeezed out within the bag-like portion 3d by the operation as shown in FIG. 3, namely, by taking out the swab X from the mixing container Y while applying a finger pressure to the constricted portion 3c in a state that the soft synthetic resin-made sponge 2 of the swab X is inserted in the constricted portion 3c of the mixing container Y.

The aqueous sodium hydroxide solution A that is used for the pretreatment method of saliva according to the present invention exerts mucin in saliva or glucan present in an outer membrane of *Streptococcus mutans* to suppress the agglutination of *Streptococcus mutans* and make the movement of the *Streptococcus mutans* as an antigen in a porous membrane easy. In this connection, an aqueous solution containing sodium carbonate or disodium hydrogenphosphate is not suitable so that the examination of *Streptococcus mutans* cannot be accurately carried out. This is because it is estimated that an alkaline aqueous solution other than the aqueous sodium hydroxide solution possibly injures the structure of the antigen of *Streptococcus mutans*.

Further, the acidic aqueous solution B that is used for the pretreatment method of saliva according to the present invention suppresses the chaining of the *Streptococcus mutans*, thereby making the movement of the *Streptococcus mutans* as an antigen in a porous membrane easy. As the acidic aqueous solution B, the most suitable is an aqueous solution containing tartaric acid and/or citric acid. However, aqueous solutions of other acids such as hydrochloric acid, sulfuric acid, nitric acid, acetic acid, lactic acid, and maleic acid are not suitable and it is difficult to obtain a target sensitivity of the examination even by a combination of the aqueous sodium hydroxide solution A. This is because it is estimated that an acidic aqueous solution other than the aqueous solution containing tartaric acid and/or citric acid possibly injures the structure of the antigen of *Streptococcus mutans*. In the pretreatment method of saliva according to the present invention, since a neutralization reaction takes place between the aqueous sodium hydroxide solution A and the acidic aqueous solution B, it is preferred to use a buffering agent. The aqueous solution containing tartaric acid and/or citric acid preferably contains tris(hydroxymethyl)aminomethane as the buffering agent. In order to effectively obtain the buffer action, though it is necessary to use the tris(hydroxymethyl)aminomethane at the side of the acidic aqueous solution B, as a matter of course, it may be simultaneously used in the aqueous sodium hydroxide solution A. However, at this time, it is already confirmed that the buffer action cannot be thoroughly obtained by other buffering agents such as a combination of sodium bicarbonate and sodium carbonate and a combination of citric acid and sodium citrate.

It is preferred that each of the aqueous sodium hydroxide solution A and the acidic aqueous solution B has a concentration of 0.01 N or more. When the concentration of each of the aqueous sodium hydroxide solution A and the acidic aqueous solution B is less than 0.01 N, the respective effects tend to be hardly obtained, or clogging of the porous membrane tends to likely occur. Actually, it is advantageous from the standpoint of the examination sensitivity that the concentration is high. Further, in the pretreatment method of saliva according to the present invention, the aqueous sodium hydroxide solution A and the acidic aqueous solution B must be provided separately because they have a neutralization action.

It is preferred that either one or both of the aqueous sodium hydroxide solution A and the acidic aqueous solution B that are used in the pretreatment method of saliva according to the present invention are mixed with a nonionic surfactant and/or an ampholytic surfactant such that proteins present on the surface of the *Streptococcus mutans* are solubilized, whereby the *Streptococcus mutans* can smoothly pass through the porous membrane. In the immunochromatographic method, ionic surfactants have hitherto been often used such that a sample solution or an antigen solution can smoothly move within an examination instrument. However, it is confirmed from the experimental results that the surfactant to be used in the pretreatment method of saliva according to the present invention for identification and quantitation of *Streptococcus mutans* must be a nonionic surfactant and/or an ampholytic surfactant and that when an anionic surfactant such as sodium lauryl sulfate and sodium dodecylbenzenesulfonate is used, it is impossible to detect the antigen by the specific antibody.

The surfactant that is used in the pretreatment method of saliva according to the present invention is not particularly limited so far as it is a nonionic surfactant and/or an ampholytic surfactant, but any of those that are generally used as a solubilizing agent of membrane proteins can be used. However, there is a difference in the detection sensitivity to the *Streptococcus mutans* antigen depending on the kind of the nonionic surfactant and/or the ampholytic surfactant to be used. Of these, one or two or more members selected from the group consisting polyethylene glycol monooctylphenyl ether, n-octyl-β-D-glucoside, n-heptyl-β-D-thioglucoside, n-octyl-β-D-thioglucoside, nonyl phenoxypolyethoxy ethanol, octyl phenoxypolyethoxy ethanol, and polyoxyethylene sorbitan monooleate are preferred as the nonionic surfacatant; and one or two or more members selected from the group consisting of 3-[(3-cholamidopropyl)-dimethylammonio]-1-propane sulfonate and 3-[(3-cholamidopropyl)dimethylammonio]-1-hydroxypropane sulfonate are preferred as the ampholytic surfactant, respectively from the standpoint of the detection sensitivity.

In the case where the nonionic surfactant and/or the ampholytic surfactant is not previously mixed with either one or both of the aqueous sodium hydroxide solution A and the acidic aqueous solution B, the nonionic surfactant and/or the ampholytic surfactant may be added dropwise to and mixed with the saliva at an arbitrary time.

Since the aqueous sodium hydroxide solution A and the acidic aqueous solution B that are used in the pretreatment method of saliva according to the present invention have each an independent function, they can be added dropwise in an arbitrary order.

It is preferred that the nonionic surfactant and/or the ampholytic surfactant to be used in the pretreatment method of saliva according to the present invention is used such that the nonionic surfactant and/or the ampholytic surfactant has a concentration in a saliva sample of 0.05 to 90% by weight after the pretreatment of the saliva. When the concentration of the nonionic surfactant and/or the ampholytic surfactant in the saliva sample after the pretreatment is less than 0.05% by weight, there is no detection sensitivity by the antigen-antibody reaction. On the other hand, when it exceeds 90% by weight, the detection sensitivity by the antigen-antibody reaction is lowered, and hence, such is not suitable.

In the pretreatment method of saliva according to the present invention, the treatment is carried out by the neutralization action between the aqueous sodium hydroxide solution A and the acidic aqueous solution B such that the saliva after the pretreatment has a pH in a range from 5 to 9. This is due to the following reason. That is, since the antigen-antibody reaction is carried out within this pH range, when the pH falls outside this range, while varying depending on the specific antibody to be used, the specific antibody is separated from the antigen or has a non-specific affinity, resulting in lowering the reliability of the assay results. Thus, in order to prevent such a defect, the pH of the saliva after the pretreatment is specified above.

The saliva sample that has been subjected to the pretreatment by the pretreatment method of saliva according to the present invention can be subjected to identification and quantitation of *Streptococcus mutans* by an antigen-antibody reaction using the conventional immunochromatographic method and is also applicable to intraoral bacteria other than the *Streptococcus mutans*. The specific antibody can be obtained by the usually employed methods. For example, the specific antibody may be obtained by the establishment method of hybridoma due to cell fusion proposed by Kohler and Milstein (Kohler G, C. Milstein, "Continuous cultures of fused cells secreting antibody of predefined specificity", *Nature,* 256:495–497 (1975)), and one prepared by merely immunizing an antigen to an animal and purifying its serum may also be used.

As described above in detail, the present invention relates to a pretreatment instrument of saliva and a pretreatment method of saliva, by which during identification and quantitation of *Streptococcus mutans* in a human saliva sample by the immunochromatographic method, agglutination by mucin and chaining of *Streptococcus mutans* in the saliva can be eliminated by a simple method. The treatment instrument of saliva according to the present invention is so inexpensive that it can simply achieve the pretreatment of saliva without using a special mixing device exhibiting a strong mixing action such as an electromotive mixer and being capable of mixing even a slight amount of the saliva. Further, the pretreatment method of saliva according to the present invention is a method in which the pretreatment of saliva can be carried out rapidly and easily using the pretreatment instrument of saliva according to the present invention. Accordingly, the invention is greatly valuable in contributing to the dental field.

While the invention has been described in detail and with reference to specific embodiment thereof, it will be apparent to one skilled in the art that various changes and modifications can be made therein without departing from the spirit and scope thereof.

What is claimed is:

1. A pretreatment instrument comprising a swab and a mixing container for saliva and a treatment liquid,
    the swab comprising a stick at a front end of which is fixed a soft synthetic resin-made sponge capable of absorbing a predetermined amount or more of saliva,
    the mixing container being made of a transparent or translucent soft synthetic resin and comprising a bag-like portion formed integrally with and continuously to a constricted portion at the end of a tapering introduction portion having an opening thoroughly larger than the soft synthetic resin-made sponge of the swab, into which the soft synthetic resin-made sponge can be inserted,
    the constricted portion and the bag-like portion in the mixing container have elasticity such that the soft synthetic resin-made sponge can be squashed by a finger pressure in a state that the soft synthetic resin-made sponge is inserted within the constricted portion and the bag-like portion; and
    the constricted portion has a width such that a pressure can be applied by fingers and has a shape such that when the soft synthetic resin-made sponge of the swab is taken out in a squashed state by the finger pressure, a minimum amount necessary for the pretreatment of saliva or more amount of the saliva can be squeezed out.

2. The pretreatment instrument according to claim 1, wherein the soft synthetic resin-made sponge is an open-cell sponge having a cell diameter of 50 to 400 μm.

3. The pretreatment instrument according to claim 1 or 2, wherein a lower limit line as a standard of a minimum amount of the liquid accommodated within the bag-like portion necessary for the pretreatment of saliva is provided in a position with a predetermined distance from a bottom portion of the bag-like portion.

4. A pretreatment method of saliva for identification and quantitation of *Streptococcus mutans* by an immunochromatographic method, which comprises
    inserting a swab comprising a stick at a front end of which is fixed a soft synthetic resin-made sponge having saliva absorbed therein into a bag-like portion of a mixing container made of a transparent or translucent soft synthetic resin,
    the mixing container comprising the bag-like portion formed integrally with and continuously to a constricted portion at the end of a tapering introduction portion having an opening thoroughly larger than the soft synthetic resin-made sponge of the swab;
    adding dropwise either an aqueous sodium hydroxide solution or an acidic aqueous solution from the opening into the mixing container;
    applying a finger pressure to the bag-like portion and squashing the soft synthetic resin-made sponge, thereby mixing the saliva with the liquid added dropwise;
    taking out the swab from the mixing container while applying a finger pressure to the constricted portion, thereby squeezing out the liquid absorbed in the soft synthetic resin-made sponge within the bag-like portion; and
    adding dropwise the aqueous sodium hydroxide solution or the acidic aqueous solution that was not added previously thereto from the opening within the mixing container and mixing therewith.

5. A pretreatment method of saliva for identification and quantitation of *Streptococcus mutans* by an immunochromatographic method, which comprises
    inserting a swab comprising a stick at a front end of which is fixed a soft synthetic resin-made sponge having saliva absorbed therein into a bag-like portion of a mixing container made of a transparent or translucent soft synthetic resin,
    the mixing container comprising the bag-like portion formed integrally with and continuously to a constricted portion at the end of a convergent introduction portion having an opening thoroughly larger than the soft synthetic resin-made sponge of the swab;
    adding dropwise either an aqueous sodium hydroxide solution or an acidic aqueous solution from the opening into the mixing container;
    applying a finger pressure to the bag-like portion and squashing the soft synthetic resin-made sponge, thereby mixing the saliva with the liquid added dropwise;
    adding dropwise the aqueous sodium hydroxide solution or the acidic aqueous solution thereto that was not added previously from the opening within the mixing container and mixing therewith; and taking out the swab from the mixing container while applying a finger pressure to the constricted portion, thereby squeezing out the liquid absorbed in the soft synthetic resin-made sponge within the bag-like portion.

6. The pretreatment method of saliva according to claim 4 or 5, wherein an aqueous solution further mixed with a pH indicator having a color transition range at a pH from 5 to 9 is used as the aqueous sodium hydroxide solution or the acidic aqueous solution.

7. The pretreatment method of saliva according to claim 4 or 5, wherein a pH indicator having a color transition range at a pH from 5 to 9 is added dropwise and mixed after the dropwise addition of either one of the aqueous sodium hydroxide solution or the acidic aqueous solution but prior to the dropwise addition of the other of the aqueous sodium hydroxide solution or the acidic aqueous solution.

8. The pretreatment method of saliva according to claim 6, wherein the pH indicator having a color transition range at a pH from 5 to 9 is one member selected from the group consisting of Methyl Red, azolitmin, p-nitrophenol, m-nitrophenol, Bromocresol Purple, Bromophenol Red, Chlorophenol Red, Phenol Red, Neutral Red, Bromothymol Blue, phenolphthalein, and Thymolphthalein.

9. The pretreatment method of saliva according to claim 4, wherein the aqueous sodium hydroxide solution or the acidic aqueous solution is an aqueous solution further mixed with a nonionic surfactant and/or an ampholytic surfactant.

10. The pretreatment method of saliva according to claim 4, wherein a nonionic surfactant and/or an ampholytic surfactant is added dropwise and mixed at an arbitrary timing.

11. The pretreatment method of saliva according to claim 9, wherein the acidic aqueous solution is a tris(hydroxymethyl)aminomethane buffer solution containing tartaric acid and/or citric acid, and the nonionic surfactant and/or the ampholytic surfactant is one or two or more members selected from the group consisting polyethylene glycol monooctylphenyl ether, n-octyl-.beta.-D-glucoside, n-heptyl-.beta.-D-thioglucoside, n-octyl-.beta.-D-thioglucoside, nonyl phenoxypolyethoxy ethanol, octyl phenoxypolyethoxy ethanol, polyoxyethylene sorbitan monooleate, 3-[(3-cholamidopropyl)-dimethylammonio]-1-propane sulfonate, and 3-[(3-cholamidopropyl)-dimethylammonio]1-hydroxypropane sulfonate.

12. The pretreatment method of saliva according to claim 5, wherein the aqueous sodium hydroxide solution or the acidic aqueous solution is an aqueous solution further mixed with a nonionic surfactant and/or an ampholytic surfactant.

13. The pretreatment method of saliva according to claim 5, wherein a nonionic surfactant and/or an ampholytic surfactant is added dropwise and mixed at an arbitrary timing.

* * * * *